United States Patent [19]

Chirikjian

[11] 4,119,521
[45] Oct. 10, 1978

[54] FLUORESCENT DERIVATIVES OF ACTIVATED POLYSACCHARIDES

[75] Inventor: Jack G. Chirikjian, Rockville, Md.
[73] Assignee: Stephen Turner, Towson, Md.
[21] Appl. No.: 790,384
[22] Filed: Apr. 25, 1977
[51] Int. Cl.² ............................................. G01N 27/26
[52] U.S. Cl. ............................ 204/299 R; 204/180 G; 260/97; 536/112
[58] Field of Search ............. 204/180 G, 299; 260/97; 536/112

[56] References Cited

U.S. PATENT DOCUMENTS

| 4,011,205 | 3/1977 | Dean et al. | 536/112 X |
| 4,020,268 | 4/1977 | Nishikawa et al. | 536/112 X |

OTHER PUBLICATIONS

Cawley, "Electrophoresis and Immunoelectrophoresis," Little, Brown & Co. (1969), pp. 200-203 & 337 & 338.

Primary Examiner—Arthur C. Prescott
Attorney, Agent, or Firm—Kane, Dalsimer, Kane, Sullivan and Kurucz

[57] ABSTRACT

The disclosure is of fluorescent deoxyribonucleic acid intercalating agent derivatives of activated polysaccharides such as cyanogen halide-activated agarose and the like. The derivatives are useful fluorescent stain ingredients of water-insoluble gels used to fractionate deoxyribonucleic acids and deoxyribonucleic acid fragments by gel electrophoresis techniques. As ingredients of electrophoretic grade gels, the derivatives of the invention function as fluorescent stains to provide direct visualization of the deoxyribonucleic acids and their fractions, under the excitation of shortwave, ultraviolet radiation.

17 Claims, No Drawings

FLUORESCENT DERIVATIVES OF ACTIVATED POLYSACCHARIDES

BACKGROUND OF THE INVENTION

1. Field of the Invention

The invention relates to derivative compounds of activated polysaccharides and more particularly relates to water-insoluble, activated polysaccharides coupled to fluorescent deoxyribonucleic acid intercalating agents and to the use of such derivative compounds as fluorescent stains to detect deoxyribonucleic acid and deoxyribonucleic acid fragments.

2. Brief Description of the Prior Art

Prior hereto ethidium bromide has been used as a fluorescent stain to detect the presence of deoxyribonucleic acid and fragments thereof separated by gel electrophoresis techniques. The stain has been used by adding it directly to the buffer used in the electrophoresis apparatus, by soaking the electrophoresis gel after electrophoretic separation of the fragments and by admixing the stain with the gel prior to electrophoresis; see for example Sugden et al, Analytical Biochemistry, 68, 36-46 (1975) and Sharp et al, Biochemistry, 12, No. 16, 3055-9 (1973). Those skilled in the art appreciate that the handling and disposal of free ethidium bromide poses hazards to the operator and others subject to exposure since ethidium bromide has been identified as a potential carcinogen. In general, other fluorescent stains capable of intercalating with deoxyribonucleic acids or fragments thereof pose special problems of handling, i.e.; toxicity, allergenicity and like problems.

The novel compounds of the present invention include a bound-up, but functionally active, fluorescent deoxyribonucleic acid intercalating agent as a fluorescent stain. The agent is chemically bound, i.e.; covalently bonded through chemical groups (such as amine groups) to the polysaccharide component and will not diffuse or wash from the gel as will the prior art physical mixes of gels with such agents. For example, in those compounds binding an ethidium halide as the intercalating agent, the ethidium halide is not diffused or washed from its chemical binding, resulting in a reduction of exposure hazard to the electrophoresis operator and others concerned with disposal of the used agent. The derivative compounds of the invention are further advantageous in that they may be readily included with electrophoresis grade gels such as agarose gels, agarosepolyacrylamide gels and the like by simple admixture therewith. There is an avoidance of separate steps of staining the electrophoretic gel before or after use. This has heretofore been a time consuming procedure which sometimes results in diffusion of the deoxyribonucleic acid bands fractionated on the gel surface. The use of the novel derivative compounds of this invention as stain ingredients in electrophoretic gels also appears to provide better resolution of the fractionation, a particular advantage for example in two dimensional electrophoresis procedures.

The derivative compounds of the invention, when used as ingredients of electrophoretic grade gels as described more fully hereinafter do not appear to reduce the mobility of deoxyribonucleic acids or fragments thereof on the gels during electrophoresis nor do they appear to otherwise interfere with or adversely affect the desired electrophoretic fractionation.

SUMMARY OF THE INVENTION

The invention comprises the reaction product of a fluorescent deoxyribonucleic acid intercalating agent and a water-insoluble, activated polysaccharide. The product of the invention is useful as a fluorescent stain to identify deoxyribonucleic acid (hereinafter referred to at times as "DNA") and deoxyribonucleic acid fragments separated on electrophoretic gel media.

The invention also comprises polysaccharide gel compositions for use in the separation of DNA and DNA fragments by electrophoresis techniques and which include the product of the invention, described above, as a fluorescent stain ingredient. The gel compositions of the invention are usefully employed in the method of the invention, to provide electrophoresis gel columns and slabs and as media for two dimensional electrophoresis procedures.

The invention also comprises a method of identifying deoxyribonucleic acid and deoxyribonucleic acid fragments separated by electrophoresis on an electrophoretic gel matrix which comprises; providing a fluorescent stain which comprises the reaction product of a fluorescent deoxyribonucleic acid intercalating agent and a water-insoluble, activated polysaccharide; dispersing said stain in an electrophoretic gel matrix; fractionating deoxyribonucleic acids, deoxyribonucleic acid fragments or mixtures thereof on said matrix by electrophoresis; and observing the fractions separated.

The term "activated polysaccharide" as used throughout the specification and claims means a polysaccharide which has been chemically modified so as to couple covalently with a DNA intercalating agent possessing functional groups capable of participating in the covalent bonds.

DETAILED DESCRIPTION OF THE INVENTION

Water-insoluble, activated polysaccharides are generally well known materials as is their preparation. They are generally prepared by the activation of water-insoluble polysaccharides or derivatives thereof containing hydroxyl groups. Examples of water-insoluble polysaccharides or derivatives thereof containing hydroxyl groups are natural vegetable fibers such as cotton, linen, jute or manilla hemp; cellulose fibers such as regenerated fibers (e.g. viscose rayon); cellulose derivatives such as carboxymethylcellulose, phosphocellulose, sulfomethylcellulose, sulfoethylcellulose, para-aminobenzylcellulose, aminoethylcellulose, diethylaminoethylcellulose, triethylaminoethylcellulose; cross-linked gels of dextran-epichlorohydrin (hereinafter referred to for convenience as "dextran gel"); dextran gel derivatives such as carboxymethyl dextran gel, diethylaminoethyldextran gel or sulfoethyldextran gel; and agar. Commercially available dextran gels having various degrees of cross-linking, i.e.; Sephadex (Pharmacia Fine Chemicals) may also be employed.

Techniques for activating polysaccharide gels are also well known. For example, the polysaccharide gels may be activated by reaction with sodium metaperiodate and stabilized by further treatment; see U.S. Pat. No. 3,947,352. Activation may also be accomplished by reacting the polysaccharide with an epoxy compound such as 1,4-bis-(2,3-epoxypropoxy) butane. The most widely followed technique for activating water-insoluble polysaccharides is probably by reaction with a cyanogen halide; see U.S. Pat. No. 3,914,183.

Preferred activated polysaccharide starting material used in the present invention is an activated, water-insoluble agarose. Agarose is a neutral galactose polymer, occurring in agar. The activated agarose preferably employed is a cyanogen halide activated agarose; see U.S. Pat. No. 3,914,183. Such materials are commercially available, for example, under the tradename "CNBr-activated Sepharose 4B" (Pharmacia Fine Chemicals).

Deoxyribonucleic acid intercalating agents lending fluorescence are also generally well known compounds as is their preparation. The agents used in the present invention have functional chemical groups in their structure capable of participating in the formation of a chemical bond with the above-described activated polysaccharides. Representative of such agents are acriflavine, acriflavine hydrochloride and like acridine derivatives and the ethidium bromide (homidium bromide). The ethidium halides are preferred fluorescent intercalating agents for DNA and ethidium bromide is most preferred in the present invention as the intercalating agent.

In general, the fluorescent DNA intercalating agents may be coupled to the activated polysaccharide by simply bringing the reactants together with stirring at a temperature within the range of from about 4° to about 55° C., preferably at room temperatures. The proportions of reactants is not critical. In general, from about 0.001 parts to about 20 parts by weight of intercalating agent for each 100 parts of activated polysaccharide is adequate to prepare stain products of the invention. Those skilled in the art will appreciate that precise proportions of the reactants required will depend on the degree of polysaccharide activation. Adjustment of proportions may be made depending on the degree of activation of the polysaccharide. If an excess of intercalating agent is provided in the reaction mixture, i.e.; more than will couple with the activated polysaccharide, the excess may be washed away after completion of the coupling reaction.

When the intercalating agent is an ethidium halide the proportion of halide is preferably within the range of from about 0.01 to about 6 parts (most preferably 0.05 to 1) by weight per 100 parts of the activated polysaccharide.

The polysaccharide-intercalating agent reactants, once brought together, are advantageously mixed with conventional and appropriate stirring apparatus. The reaction between intercalating agent and activated polysaccharide is generally complete in about 1 hour when carried out at room temperature. Shorter reaction times are experienced at higher temperatures and longer periods at lower temperatures as will be appreciated. At the end of the reaction period, excess, uncoupled intercalating agent may be separated by washing the resultant gel with a saturated salt solution followed by an alcohol wash, preferably employing isopropanol. The washed gel may then be used immediately according to the method of the invention or it may be freeze-dried in the presence of lactose as a stabilizer and stored for future use. The freeze-dried product may be stored for at least a year, in the absence of light and preferably at a temperature of below circa 8° C. To use the freeze-dried product, the compound is rehydrated with an aqueous buffer or slightly acid (pH circa 8) aqueous solution.

The fluorescent DNA intercalating agent/water-insoluble activated polysaccharide products described above are usefully employed as fluorescent DNA stains by simple admixture with electrophoresis grade gels such as agarose, hybrid gels comprising mixtures of agarose with polyacrylamide and like gels. The fluorescent stain material of the invention is readily incorporated within electrophoresis grade gels by heating the gel to a melting temperature and admixing the melted gel with stain ingredient of the invention. After mixture, the resulting gel may be cast in any conventional gel mold and the cast composition allowed to cool to a gelling temperature. Advantageously, the proportion of stain ingredient employed in the gel compositions of the invention is within the range of from about 0.001 to about 10 parts by weight per 100 parts of the electrophoresis grade gel employed to make the gel compositions of the invention. Lower proportions generally result in poor visibility of the DNA fractions following electrophoresis while higher proportions may be detrimental to background resolution. When the stain ingredient is the preferred product of an activated agarose and an ethidium halide such as ethidium bromide, the preferred proportion of the product as the active stain ingredient in an electrophoresis grade gel is within the range of from about 0.1 to about 1.0 (most preferably 0.5) parts per 100 parts of the electrophoresis grade gel.

The product gels including the stain ingredients of the invention may be usefully employed as electrophoresis columns, slabs and the like by casting in appropriate molds and using in conventional electrophoresis apparatus using conventional separation techniques.

The following examples describe the manner and process of making and using the invention and set forth the best mode contemplated by the inventor of carrying out the invention, but are not to be construed as limiting. All parts are by weight unless otherwise specified.

EXAMPLE 1

About 250 parts of freeze dried cyanogen bromide activated agarose beads (CNBr-activated Sepharose 4B, Pharmacia Fine Chemicals Incorporated, Piscataway, New Jersey) are washed and reswollen on a sintered glass filter with 1mM hydrochloric acid. An appropriate vessel is then charged with 100 parts of the washed gel so obtained. To the gel there is added with stirring, 0.05 parts of ethidium bromide dissolved in sodium bicarbonate buffer (0.1M pH 8.3). Stirring is continued for about 1 hour at room temperature (circa 26° C.). At the end of this period, the reaction product is washed with a saturated solution of sodium chloride and then with isopropanol to remove excess, unbound ethidium bromide. The unremoved ethidium bromide is covalently bonded to the cyanogen bromide activated agarose.

As evidence that the ethidium halide is covalently bonded to the polysaccharide gel, one will note the inability to remove all of the ethidium halide employed as starting material by diffusion, washing with high salt content solutions, alcohols or by electrophoresis. The resulting gel is removed and stored in the dark at a temperature of circa 4° C. The gel so obtained is a cyanogen bromide activated agarose coupled to ethidium bromide.

Similarly, repeating the above procedure but replacing the activated agarose with any other activated polysaccharide described above, a fluorescent stain of the invention is obtained. Also, repeating the above procedure but replacing the ethidium bromide used therein with an equal proportion of any other fluorescent intercalating agent, a fluorescent stain of the invention is likewise obtained.

EXAMPLE 2

An appropriate vessel is charged with 20 parts of agarose gel and the charge is melted by heating to a melting temperature (circa 65° C.). To the melted agarose there is added with stirring 0.1 parts of the stain ingredient obtained in Example 1, supra. The resulting mixture is cast in a slab gel mold and allowed to cool to room temperature to obtain an electrophoresis grade slab gel.

Similarly, repeating the above procedure but replacing the agarose gel with any other electrophoresis grade gel, a composition of the invention is obtained. Also, replacing the stain ingredient used above with an equal proportion of any other stain ingredient of the invention will produce a composition of the invention.

EXAMPLE 3

The digestion of 1.0 μg of lambda DNA is carried out in 20 ml of a mixture of 50 mM of hydroxymethylaminomethane hydrochloride (pH 7.5, Tris hydrochloride, Bethesda Research Laboratories Inc., Rockville, Maryland 20850), 5 mM of magnesium chloride, 1 mM of dithiothreitol, 100 μg/ml autoclaved gelatin and 2 units of restriction endonuclease (Endo R . Hae III, Bethesda Research Laboratories Inc., supra.) at 37° C. for 1 hour. To the digest there is added 15 μl of a solution of 50 percent sucrose and 0.2 percent bromophenol blue and the resulting mixture is loaded on the agarose slab gel of Example 2, supra. Electrophoresis is carried out using the apparatus of Studier, J. Mol. Biology, 79, 237 (1973) at 175 volts, 50 ma for 1.25 hours at room temperature. At the end of this time the separated DNA fractions may be visualized on the slab gel by exposing it to short wave, ultraviolet light. The DNA intercalated ethidium bromide, bound to the agarose gel, fluoresces. The bands are clearly resolved and visible.

What is claimed:

1. The chemical reaction product of a fluorescent deoxyribonucleic acid intercalating agent and a water-insoluble, activated polysaccharide wherein said agent has formed a chemical bond with the activated polysaccharide.

2. The product of claim 1 wherein said agent is an ethidium halide.

3. The product of claim 2 wherein said halide is ethidium bromide.

4. The product of claim 1 wherein said polysaccharide is agarose.

5. The product of claim 1 wherein said activated polysaccharide is a cyanogen halide activated agarose.

6. The product of claim 3 wherein said activated polysaccharide is cyanogen bromide activated agarose.

7. The product of claim 1 wherein the proportion of said agent employed in the reaction is within the range of from about 0.001 to about 20 parts by weight per 100 parts of said polysaccharide.

8. The product of claim 2 wherein the proportion of said halide in the reaction is within the range of from about 0.01 to about 6 parts per 100 parts by weight of said polysaccharide.

9. Gel composition useful in the electrophoretic separation of deoxyribonucleic acid and deoxyribonucleic acid fragments, which comprises; in admixture, an electorphoresis grade gel and the stain reaction product of a fluorescent deoxyribonucleic acid intercalating agent and a water insoluble, activated polysaccharide wherein said agent has formed a chemical bond with the activated polysaccharide.

10. The gel composition of claim 9 wherein said electrophoresis grade gel is a polysaccharide.

11. The gel composition of claim 10 wherein said polysaccharide is agarose.

12. The gel composition of claim 10 wherein said agent is ethidium bromide.

13. The gel composition of claim 11 wherein said agent is ethidium bromide.

14. The gel composition of claim 9 wherein the proportion of stain reaction product is within the range of from about 0.001 to about 10 parts per 100 parts by weight of the electrophoresis grade of gel.

15. The gel composition of claim 13 wherein the proportion of stain reaction product is within the range of from about 0.1 to about 1.0 parts per 100 parts by weight of agarose.

16. The product of claim 1 wherein said agent is an ethidium halide and said activated polysaccharide is a cyanogen halide activated dextran gel.

17. A gel composition of claim 9 wherein said electrophoresis grade gel is a cyanogen halide activated dextran gel and said agent is an ethidium halide.

* * * * *